US011134870B2

(12) United States Patent
Lieb et al.

(10) Patent No.: US 11,134,870 B2
(45) Date of Patent: Oct. 5, 2021

(54) IN VIVO SENSOR

(71) Applicant: Envivo Diagnostics, LLC, Denville, NJ (US)

(72) Inventors: Stephen J. Lieb, Denville, NJ (US); Kalle Levon, Brooklyn, NY (US); Kenneth D. Warner, Fairfield, CT (US)

(73) Assignee: EnVivo Diagnostics, LLC, Denville, NJ (US)

( * ) Notice: Subject to any disclaimer, the term of this patent is extended or adjusted under 35 U.S.C. 154(b) by 193 days.

(21) Appl. No.: 16/405,425

(22) Filed: May 7, 2019

(65) Prior Publication Data
US 2020/0069227 A1 Mar. 5, 2020

Related U.S. Application Data

(60) Provisional application No. 62/668,588, filed on May 8, 2018.

(51) Int. Cl.
*A61B 5/145* (2006.01)
*A61B 5/1473* (2006.01)
*A61B 5/00* (2006.01)

(52) U.S. Cl.
CPC ........ *A61B 5/14546* (2013.01); *A61B 5/0031* (2013.01); *A61B 5/1473* (2013.01); *A61B 5/14507* (2013.01); *A61B 5/686* (2013.01)

(58) Field of Classification Search
CPC ............ A61B 5/14503; A61B 5/14865; A61B 5/1473; A61B 5/14735; A61B 5/14546;
(Continued)

(56) References Cited

U.S. PATENT DOCUMENTS 7,083,578 B2 * 8/2006 Lewkowicz ....... A61B 1/00158
600/593
7,884,398 B2 * 2/2011 Levon ................ G01N 27/4148
257/236
(Continued)

FOREIGN PATENT DOCUMENTS

WO WO-2004056307 A2 * 7/2004 .............. A61P 37/02
WO WO-2006089069 A2 * 8/2006 ............. G16H 40/63
(Continued)

OTHER PUBLICATIONS

Deirmengian, Carl; Kardos, Keith; Kilmartin, Patrick; Cameron, Alexander; Schiller, Kevin; Parvizi, Javad "Combined Measurement of Synovial Fluid α-Defensin and C-Reactive Protein Levels: Highly Accurate for Diagnosing Periprosthetic Joint Infection," The Journal of Bone and Joint Surgery, vol. 96 (Year: 2014).*
(Continued)

*Primary Examiner* — Eric F Winakur
*Assistant Examiner* — Alice Ling Zou

(57) ABSTRACT

A device detects infection associated with a prosthetically implanted device, such as a prosthetic knee. The device includes a sensor to detect the presence of one or more proteins secreted by body tissues in response to infection. The sensor may include a surface with a molecular imprint of the protein connected with a potentiometric or amperometric measuring device to detect when the protein bonds with the implanted surface. The device further includes an inductive coil coupled with a corresponding coil located outside the body. Electrical power for operating the measuring device and other circuitry is provided by inductive coupling between the coils. Signals indicating whether the protein is detected are communicated from the device to the external circuitry connected with the external coil.

15 Claims, 14 Drawing Sheets

(58) Field of Classification Search
CPC ..... A61B 5/0031; A61B 5/686; A61B 5/1468; A61B 5/14507
See application file for complete search history.

(56) References Cited

U.S. PATENT DOCUMENTS

| | | | |
|---|---|---|---|
| 2002/0072720 A1* | 6/2002 | Hague | A61M 5/158 604/264 |
| 2005/0049472 A1* | 3/2005 | Manda | A61B 5/14865 600/345 |
| 2006/0047283 A1* | 3/2006 | Evans, III | A61F 2/38 606/102 |
| 2010/0204551 A1* | 8/2010 | Roche | A61B 5/4839 600/301 |
| 2012/0209090 A1* | 8/2012 | Goodall | A61B 5/14503 600/309 |

FOREIGN PATENT DOCUMENTS

| | | | | |
|---|---|---|---|---|
| WO | WO-2008035089 A1 | * | 3/2008 | ........... A61B 5/0031 |
| WO | WO-2010048627 A2 | * | 4/2010 | ......... G01N 33/5436 |
| WO | WO-2012158202 A2 | * | 11/2012 | ........... A61B 5/1473 |
| WO | WO-2014179398 A1 | * | 11/2014 | ........... A61K 9/0097 |

OTHER PUBLICATIONS

Lyu, Hong-Kun; Choi, Young-Sam; Shin, Jang-Kyoo; Kim, Jae-Hyun "A commercial MOSFET-based biosensor with a gold extended gate electrode," Proc. SPIE 7313, Smart Biomedical and Physiological Sensor Technology VI, 73130S (Year: 2009).*

Salvo, Pietro; Dini, Valentina; Kirchhain, Arno; Janowska, Agata; Oranges, Teresa; Chiricozzi, Andrea; Lomonaco, Tommaso; Di Francesco, Fabio; Romanelli, Marco "Sensors and Biosensors for C-Reactive Protein, Temperature and pH, and Their Applications for Monitoring Would Healing," Sensors, vol. 17 (Year: 2017).*

* cited by examiner

IN VIVO SENSOR

This application claims priority under 35 U.S.C. § 119 to U.S. Provisional Patent Application No. 62/668,588, filed May 8, 2018, which is incorporated herein by reference.

BACKGROUND

Field

The present disclosure relates to an implantable sensor to detect an infection. In particular, the present disclosure describes a sensor for implantation along with a prosthetic joint replacement that monitors the bodily fluid surrounding the joint and alerts the user and/or the user's physician if biochemical indicators of infection are detected.

Background of the Invention

Partial and total joint replacement surgeries are becoming increasingly common in developed countries such as the United States. It is estimated that in the United States more than 5 million individuals have had a partial or total knee replacement and more than 3 million have had hip replacement surgery. The prevalence of joint replacement is growing as the population ages.

The incidence of infection occurring in hospitalized patients is a significant public health problem. Post-surgical infection increases the cost of treating patients and leads to significant suffering and morbidity. Joint replacement surgery exposes patients to a high risk of infection. Joint replacement surgeries typically involve large incisions to expose bone and tissue around the diseased joint. Bone and cartilage must typically be removed in order to fit the prosthetic joint in place. Exposing tissues that have low blood supply, such as bone and cartilage, poses a particular risk of infection, in part because such tissues are difficult to treat with systemic antibiotics. Low blood supply means that the amount of an antibiotic agent reaching these tissues is reduced.

In approximately 1-2% of all knee replacement surgeries in the United States, post-surgical infection around the periprosthetic implant, resulting in a periprosthetic joint infection (PJI). The source of the infectious may be the introduction of infectious organisms into the surgical field during the implantation surgery. Infection may also occur because infectious agents enter the surgical wound post-operatively, through sutured closures or drains. Infections associated with the prosthesis may also occur due to a systemic infection introduced at a location on the patient's body remote from the surgical site, or from infectious organisms chronically resident in the patient's tissues that finds its way to the prosthetic device. The prosthetic device serves as a nidus for infection.

PJI can be treated with systemic antibiotics or with localized injection of antibiotics near the prosthesis if treatment begins at the early stages of the infection. As mentioned above, treatment of infection in tissues such as bone, that are not well vascularized can be difficult. Nonetheless, early treatment of such infections using antibiotics injected at the site of the implant or systemically has been shown to be effective. Unfortunately, a PJI may not exhibit symptoms that can be noticed by the patient or the patient's physician at an early stage. Symptoms such as swelling, pain, and stiffness are commonly associated with a normal surgery. In some cases, it is not until the surgical trauma has healed that a patient may notice pan caused by PJI.

If an infection associated with a joint prosthesis is not detected at an early stage, bacteria can form a biofilm on the surface of the prosthesis. Once an infectious organism sets up a biofilm, treatment by injection of antibiotic agents becomes less effective. The biofilm creates a micro-environment sealed off from the exchange of body fluids. As a result, systemic or localized antibiotics cannot reach organisms embedded in the biofilm.

In the case where infection of a joint prosthesis has progress to the point where a biofilm is established, one course of treatment is to reopen the surgical site and apply antibiotic agents directly to the surface of the prosthesis. This is expensive, traumatic to the patient, and can delay the healing of tissues surrounding the surgical site. Also, a second surgery provides another opportunity for organisms to infect the prosthesis.

Another course of treatment is the complete removal of the prosthesis as well as infected bone and soft tissue, followed by the application of antibiotic agents, such as antibiotic bone cement, to the infected tissue. Typically, a period of several months is required to allow the antibiotic agents to act on the infected tissue. A new prosthetic device is then implanted. Unfortunately, very often infection reoccurs.

In addition to infection, patients can be injured because materials forming the prosthetic joint can leach substances, such as metal ions including cobalt, into the body. For example, so-called metal-on-metal implants have been known to cause metallosis, leading to tissue damage in some patients. Polyethylene particles created during normal wear and tear have also been implicated in joint loosening due to the action of macrophages on the particles and subsequent osteolysis. Surfaces of the implant that contact one another when the patient articulates the joint can be abraded, causing particles of material to come loose. These particles can cause irritation and an immune reaction, leading to discomfort and disease.

The problem of infections associates with prosthetic joint replacements is not limited to prosthetic knee replacements. Infections also occur in other joint prostheses, for example, hip replacements. Unless treatment for infection associated with these prostheses is started at an early stage, the consequences can be serious, including the need to revision surgery to remove and replace the infected joint.

SUMMARY

The present disclosure relates to apparatuses and methods to address these difficulties by providing an in vivo sensor that monitors a patient's synovial fluid following joint replacement surgery to detect the presence of one or more peptides, protein, or other components secreted by the body into the synovial fluid as a result of infection. According to one aspect, the present disclosure provides a device that detects the presence of the peptide α-defensin in the synovial fluid. α-defensin has been determined to be present in synovial fluid of joints experiencing PJI. The presence of α-defensin indicates, with a very high correlation and sensitivity that a joint is experiencing PJI.

According to another aspect of the disclosure, the device is equipped with a sensor for detecting the presence of a second peptide, protein, or component in the synovial fluid in combination with or in the alternative to the detection of α-defensin. One such other component is C-reactive protein (CRP). The presence of CRP is also highly correlated with PJI. When it is determined that both α-defensin and CRP are present in synovial fluid, there is an even higher degree of correlation with PJI.

According to a further aspect of the disclosure, the device is equipped with a sensor to measure the presence of inorganic substances, for example, metal ions and polymers, released from a joint prosthesis into bodily fluids, such as the synovial fluid.

According to a still further aspect of the disclosure, an implantable device is attached to a knee replacement prosthesis and an external device is provided that can be worn by the patient around the site of the prosthesis. The implanted device includes an induction coil that electromagnetically couples with an induction coil on the external device. Electrical power to operate the implanted device is provided by way of the inductive coupling between the coils. Signals from the implanted device are communicated to the external device by way of the coupled signal.

According to a still further aspect of the disclosure, an implanted device to detect PJI is connected with a prosthetic knee and provided with a surface exposed to the patient's synovial fluid when implanted. The surface is provided with a molecular imprinted material adapted to preferentially bind or otherwise interact with selected substances such as α-defensin, C-reactive protein, and the like. The surface is coupled with a charge sensitive component, such as the gate of a field-effect transistor or potentiometric sensor. Binding of the selected substances, which generally carry a negative charge when dissolved in bodily fluids, results in a signal from the potentiometric sensor or a change in current flowing through the transistor. The device detects this signal and transmits a signal indicating that the identified substance has been detected and communicates that signal to an external device.

According to a still further aspect, an array of sensors is provided on the exposed surface and the device includes circuitry to selectively read signals from selected ones of the sensors. According to a further aspect, certain sensors are adapted to detect different substances and to determine, based on signals indicating that a combination of substances is present in the bodily fluid and that combination indicates a disease state or that the disease state has changed, for example, because an infection has progressed or because an infection is being successfully treated.

According to a still further embodiment, the array of sensors is provided with a dissolvable coating, and the coating is or differing thicknesses and/or different dissolution rates over different sensors in the array. When the device is implanted, some or all of the sensors are isolated from bodily fluid. As time passes when the coating is exposed to the bodily fluid, the coating dissolves, exposing sensors sequentially to the bodily fluid. Circuitry in the device monitors the array of sensor and, as sensors become inoperative because they are completely bound by a selected substance, or covered by cells, the circuitry ceases to read signals from those sensors and instead selects sensors that are newly exposed by the dissolvable coating.

According to a still further embodiment, a sensor is provided on prostheses to replace other joints or structures, for example, hip joints, elbow joints, ankle joints, spinal structures, and the like. As with the above-described embodiments, the sensor is positioned to interact with bodily fluids surrounding the prosthetic joint and detect analytes that indicate the early onset of an infection. Signals from the implanted detector are monitored from outside the body, for example, by way of a radio frequency transmitter or coupled inductive coils. When an infectious condition is detected, a signal can be sent to the patient or the patient's physician indication that medical intervention should be considered.

According to a still further embodiment, a device that detects analytes indicative of an infection or other unhealthy condition is positioned in other areas of the body, for example, in the bladder, the sinus cavity, or in contact with a patient's bloodstream to monitor the concentration or presence of the analyte and send a signal outside the body to alert the patient or medical personnel.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
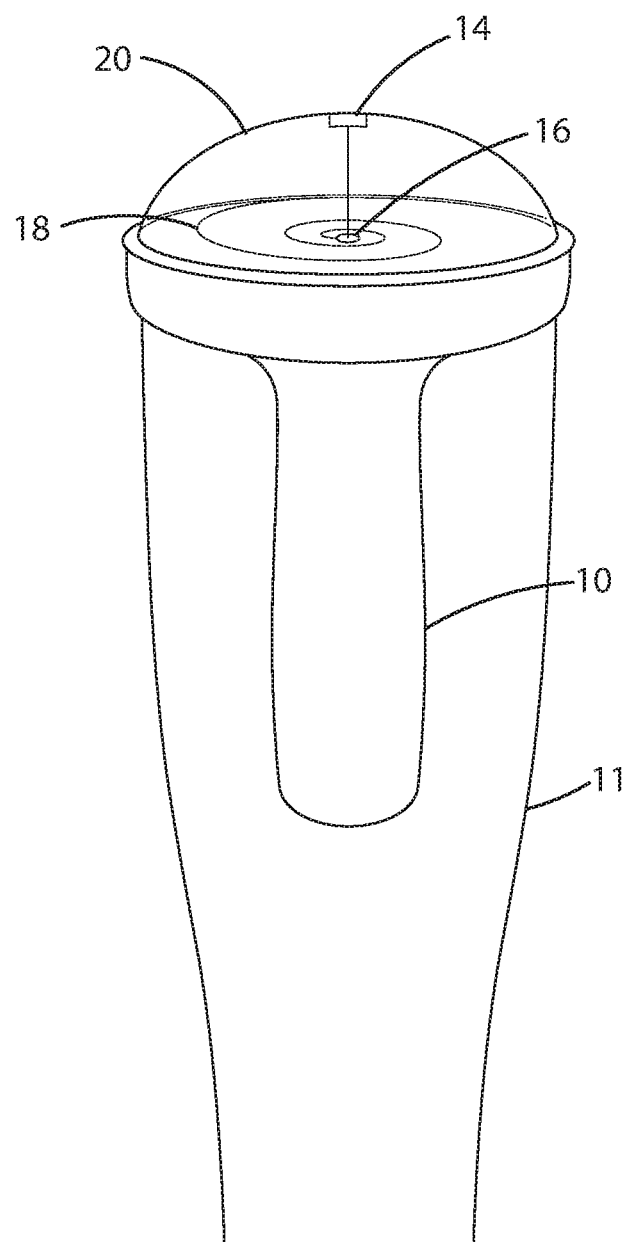
FIG. 1 is a perspective view of a portion of a knee implant according to an embodiment of the disclosure.

FIG. 1 shows the tibial portion of a prosthetic knee replacement 1. The prosthetic device 1 consists of a solid body 10 adapted to be inserted into the surgically prepared end of a patient's tibia 11. The body 10 is formed from a biocompatible material with sufficient strength and other mechanical properties to form a knee prosthesis as is known to those of skill in the relevant art. At the top end of the prosthesis 1 is an elastomeric pad 20. The pad 20 is designed to absorb impact from the corresponding femoral portion of the prosthesis (not shown) when the patient walks. Such an arrangement is well-known to those of ordinary skill in the field of prosthetic joints. The pad 20 is formed from a bio-compatible material such as Ultra High Molecular Weight Polyethylene (UHMWPE), as known by those in the relevant art. According to one embodiment, the pad 20 is formed from a polymer such as UHMWPE that is impervious to water and to body fluids. By embedding the device, described below, in a pad 20 made of a water-impermeable material, portions of the electronic circuitry 16 can be protected from interacting with the chemical and biological environment of the patient.

A prosthesis according to embodiments of the invention include sensor 14, electronic circuitry 16, and a coil 18. Coil 18 and circuitry 16 are embedded in pad 20, isolating them from contact with body fluids. Sensor 14 is affixed to the surface of the pad 20. According to one embodiment, sensor 14 is located on a portion of pad 20 that is not contacted by the femoral portion of the prosthesis so that mechanical impact between the femoral and tibial portion of the prosthetic joint do not impinge on the sensor 14 or electronics 16. According to another embodiment of the invention sensor 14 is located in a pocket formed on the surface of the pad. The pocket is arranged so that, when the patient bends his or her leg, the flexing of the femoral portion of the prosthesis relative to the tibial portion causes synovial fluid to circulate through a channel adjacent to the surface of the sensor 14. This circulation provides a flow of synovial fluid across the sensor.

Figure 2:
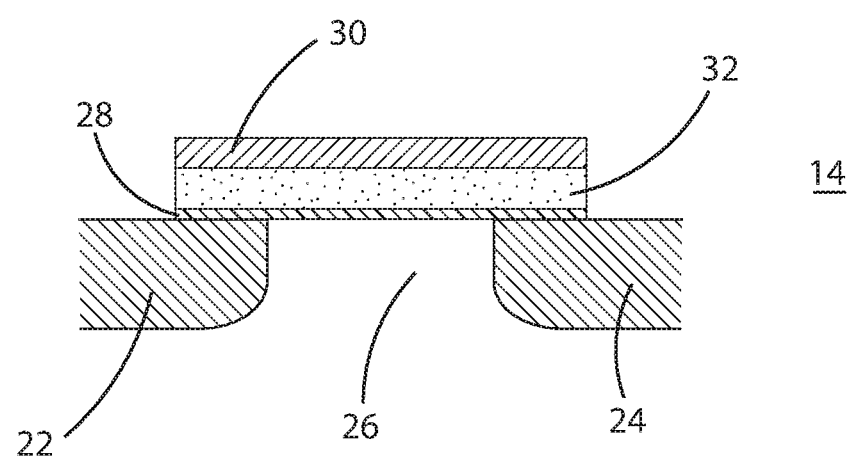
FIG. 2 is a cross section of a sensor according to an embodiment of the disclosure.

FIG. 2 shows sensor 14. According to one embodiment, sensor 14 is a floating or extended gate field effect transistor (FGFET), or a working electrode of a potentiometer. Such a device may be formed on a silicon wafer using CMOS technology or by other techniques known in the art. Sensor 14, according to one embodiment, includes a drain electrode region 22 and a source electrode region 24 formed in the bulk 26. Above the source and drains 22, 24 is an insulating layer 28. A gate 32 is formed above the insulating layer 28. On the top surface of the gate 32 is a sensing surface 30. As will be described more fully below, the sensing surface 30 includes a moiety or other physical or chemical mechanism that adsorbs selected chemical compounds from fluid in contact with the surface 30. Exemplary examples of circuitry connected with the sensor 14 to detect and communicate a signal are described below. These are provided as illustrations only and are not meant to be limiting.

Figure 3:
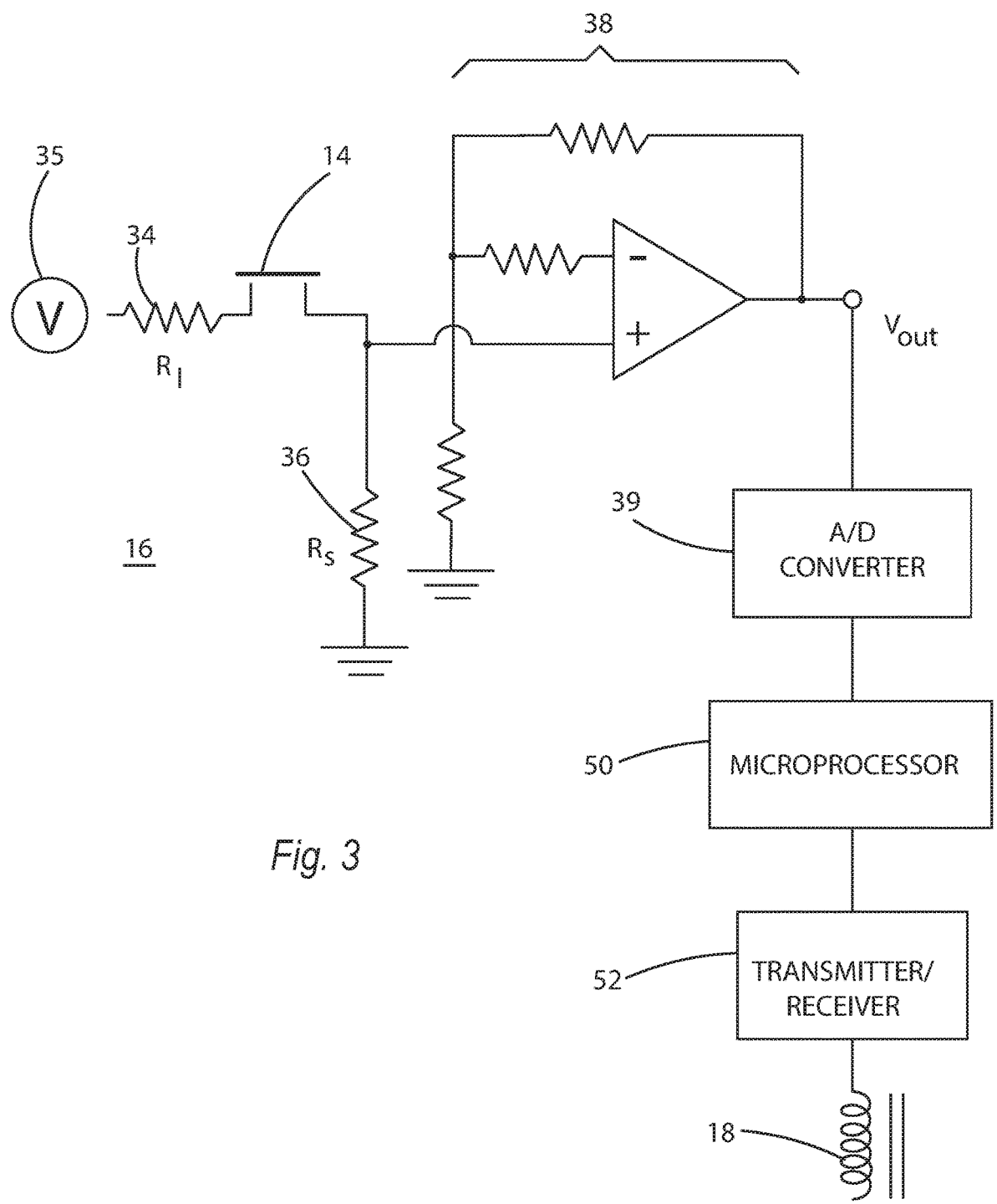
FIG. 3 is an electrical schematic according to an embodiment of the disclosure.

FIG. 3 shows a portion of circuit 16 connected sensor 14. Circuit 16 includes a voltage source 35 connected with a current limiting resistor 34. Sensor 14 is connected with current monitoring resistor 36. Resistor 36 is connected to ground. In operation, current flowing from voltage source 35 through resistor 34, sensor 14 and resistor 36 causes a voltage to develop across resistor 36. This voltage is provided to amplifier 38. According to one embodiment, amplifier 38 is a high impedance amplifier, such as an operational amplifier. An output voltage is generated by amplifier 38 that is indicative of the current flowing through the source and drain regions 22, 24. The output voltage is provided to an analog-to-digital converter 39 that provides a digital representation of the voltage to a microprocessor 50. Microprocessor 50 is connected with a transmitter/receiver circuit 52. Based on the voltage signal, the microprocessor 50 provides a signal to the transmitter/receiver 52 indicating whether a substance indicating an infection is present. Transmitter/receiver 52 provides a signal to coil 18 based on what is received from the microprocessor 50.

As will be discussed more fully below, the signal from amplifier 38 is used to detect the presence of substances that indicate an infection. Other circuitry generates an output signal that is transmitted out of the patient's body to alert the patient and the patient's healthcare provider that an infection may be present.

FIGS. 4*a*-*f* show a process for forming surface 32. Sensor substrate 402 is coated with a metallic surface, such as gold. The coated substrate 402, 404 is immersed in a buffer solution and the molecule of interest, for example, α-defensin is added to the solution. The α-defensin deposits on the gold surface. This deposition may be enhanced by applying a charge to the gold surface using a power supply (not shown). The concentration of α-defensin in the buffer solution is selected so that less than a monolayer of α-defensin deposits on the surface. According to one embodiment, the concentration is selected so that 5%-95% of the gold surface is covered. According to a preferred embodiment, 20% to 80% of the surface is covered. According to a most preferred embodiment 50% of the surface is covered with α-defensin. According to other embodiments, instead of α-defensin, another molecule of interest that is present in bodily fluid when an infection occurs may be applied to the gold surface.

Figure 4A:
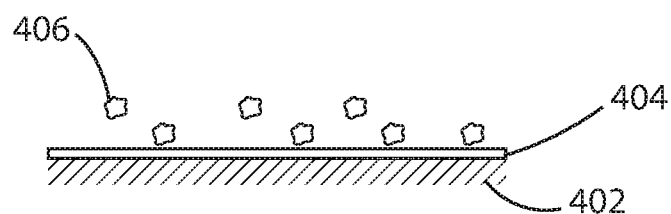
FIGS. 4a-4f illustrate a method for creating a substrate according to an embodiment of the disclosure.
Figure 4B:
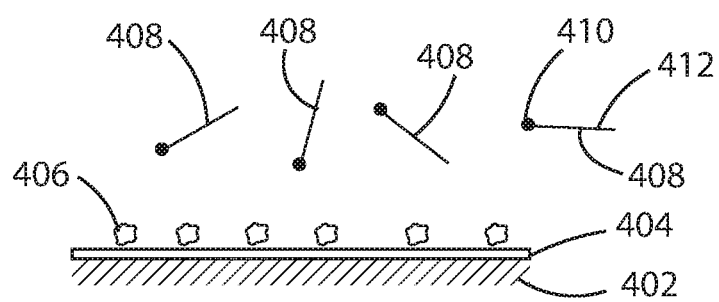
Figure 4C:
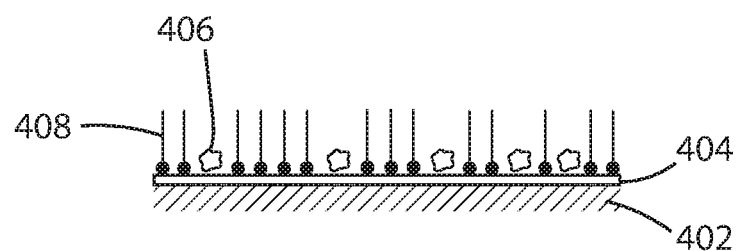

Next, as shown in FIG. 4*b*, molecules 408 including a thiol group 410 are added to the buffer. These molecules are amphiphilic, having a thiol group 410 at one end and a hydroxyl end group 412, which makes the molecule soluble in the buffer. The thiol 408 complexes with atoms of the gold surface 404 to form a self-assembled monolayer (SAM) where the thiol can contact the gold as shown in FIG. 4*c*. The tails 412 remain soluble in the buffer and align away from the gold surface. According to one embodiment, the tails 412 include unsaturated bonds. According to another embodiment, tails 412 include active groups along their length that will form hydrogen bonds with the molecule of interest. According to a further embodiment, the terminal end opposite the thiol 408 does not readily form bonds with any molecule.

Figure 4D:
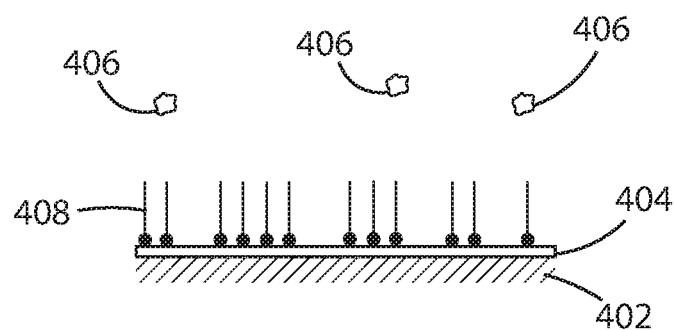
Figure 4E:
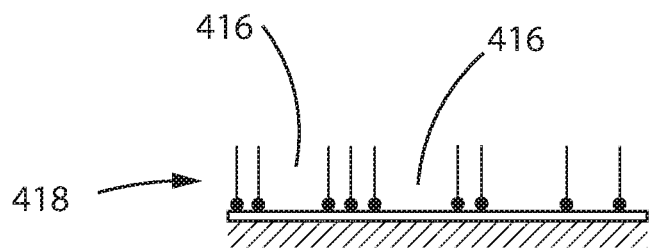

The concentration of molecules 408 is selected to be in excess of the amount required to form a monolayer on the gold surface not covered by α-defensin. According to one embodiment, the substrate is allowed to incubate in the buffer for 4 hours at 30° C. while the solution is gently stirred. As shown in FIG. 4*c*, molecules 408 form an SAM across the surface 402 except where α-defensin is deposited. Next, as shown in FIG. 4*d*, the surface is treated to remove the α-defensin molecules 406 by washing with water, an ionic solution, an enzyme such as trypsin, or combinations thereof. According to one embodiment, the α-defensin is removed by rinsing repeatedly (10×) with 1 M NaCl solution, de-adsorption overnight, and then rinsing repeatedly (3×) with water. The result, shown in FIG. 4*e* is a surface covered in a monolayer of molecules 408 with spaced 416 that conform to the shape of the α-defensin molecules 406. Tails 412 extend from the surface into the buffer. According to one embodiment, structure 418 is suitable for forming a sensing surface, such as sensing surface 32. Structure 418 could be formed, for example, on the floating gate of an FET or on a surface connected with a potentiometric measuring device such that the structure forms the working electrode for the potentiometer.

When structure 418 is exposed to a solution containing α-defensin for example, a bodily fluid around an infected periprosthetic joint, the α-defensin bonds with the exposed gold surface 404 in holes 416. Because the shape of the holes corresponds to the outline of α-defensin, that molecule will selectively bind to the surface. In addition, the active groups along the length of the tails 412 adjacent the holes 416 form hydrogen bonds with the α-defensin. Because the exposed ends of the tails 412 do not bond with any molecule, including α-defensin, the binding of α-defensin is confined to the holes 416. As a result, α-defensin will form a stable bond with the structure 418 and charge associated with the bound α-defensin can be detected by potentiometric or amperometric means. Other molecules cannot form stable bonds, or at least will form less stable bonds than α-defensin because they either are too large to fit into holes 416 or else to not conform to the edges of holes 416 and thus form fewer bonds tails 412 along the sides of holes 416.

Figure 4F:
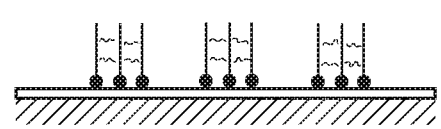

According to a further embodiment, shown in FIG. 4f, tails 412 are cross-linked with one another following the steps forming the structure in FIG. 4e. Tails 412 can include active groups that form bonds with adjacent tails. Such bonding may be facilitated by exposing the structure to a substance the activates bond formation, or by exposing the structure to ionizing radiation, including e-beam, x-rays, or gamma rays. By cross-linking tails, the monolayer structure is believed to be stabilized. And dissociation of between thiol groups and gold atoms that may occur does not result in loss of contact between the monolayer and the substrate since the adjacent cross-linked molecules 408 hold the dissociated molecule in place.

Figure 11:
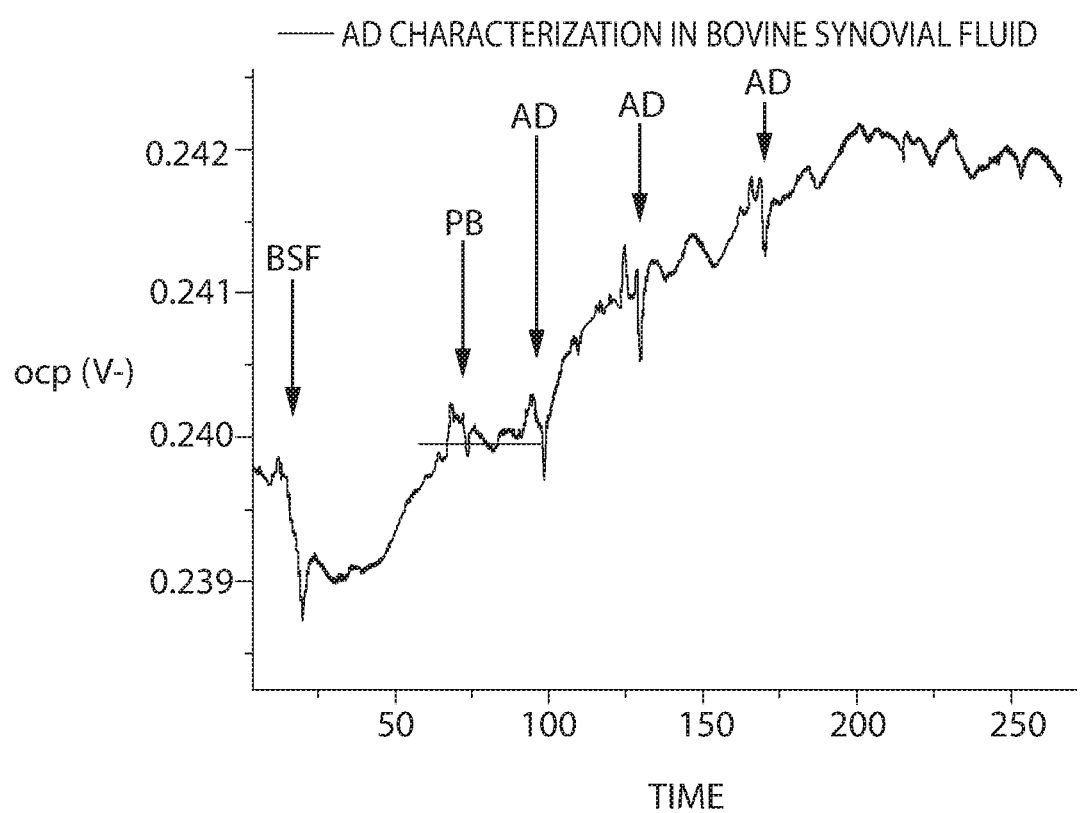
FIG. 11 shows a graph of the output of a sensor according to an embodiment of the disclosure in response to the concentration of α-defensin to a sample of bovine synovial fluid

FIG. 11 shows the response of a sensor made according to an embodiment of the disclosure in response to the presence of α-defensin. A sensor was prepared by evaporating a gold layer onto a glass substrate. The gold surface was immersed in a mixture (19:1 ratio) of α-defensin (40 ug in 10 mL deionized water, Product No. AB54409 from Abcam, Inc., Cambridge, Mass.) 4 mg 11-mercapto-1-undecanol which was dissolved in 10 ml ethanol (i.e 0.1 mM). The α-defensin was then removed by rinsing repeatedly (10×) with 1 M NaCl solution, de-adsorption overnight, and then rinsing repeatedly (3×) with water.

The gold layer was then connected with a potentiometer. The potentials of the working electrode against the reference electrode were measured with an Accumet AR15 potentiometer purchased from Fisher Scientific (Pittsburgh, Pa.) and EMF 16 channel Electrochemical Interface purchased from Lawson Labs (Malverin, Pa.). When diluted to a 1× concentration, 10× phosphate buffered saline solution purchased from Sigma Aldrich (St Louis, Mo.) yield a phosphate buffer concentration of 0.01 M and a sodium chloride concentration of 0.154 M with pH 7.4. A stable reading was recorded from the potentiometer.

A drop in potential from the initial 0.2398 mV to about 0.239 occurred when bovine synovial fluid (identified as BSF in FIG. 11) was added and the potential returned to the initial value after a few seconds. This was perhaps related to the dissolution of the synovial fluid in the buffer. A small amount of additional buffer (PB) was added with no change potential at about 0.240 mV. About 50 ul of α-defensin (AD) was added and the potential on the gold layer rose to about 0.2410 mV. An additional 50 ul of AD was added and the potential rose again, to about 0.2415 mV. An additional 50 ul of AD was added and the potential rose again, to about 0.2420 mV.

According to one embodiment, surface 32 is imprinted with α-defensin. According to a further embodiment, the device includes an array of sensors 14. Molecular imprinted surfaces 32 are applied to selective ones of the sensors 14. This may be accomplished by applying a masking layer to selected sensors while an imprinted layer 32 is applied to others of the sensors.

Figure 5A:
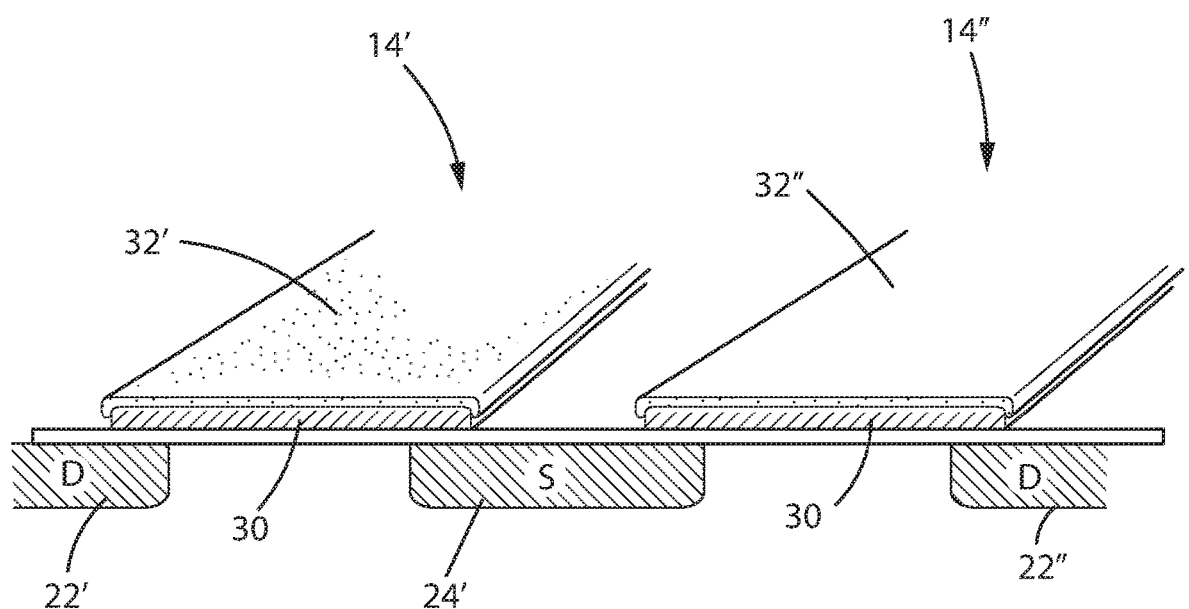
FIG. 5a shows a sensor according to an embodiment of the disclosure.
Figure 5B:
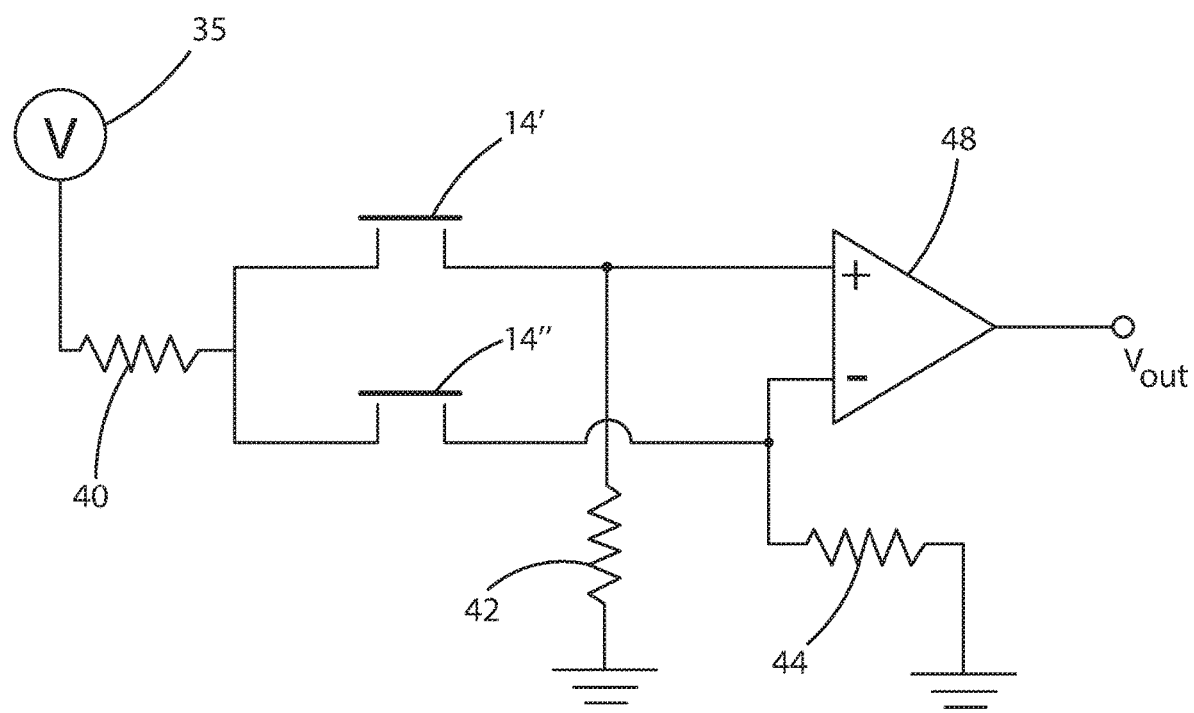
FIG. 5b is an electrical schematic according to an embodiment of the disclosure.

FIGS. 5a and 5b show a further embodiment of a sensor according to the disclosure. As shown in FIG. 5a, two sensors 14' and 14" are formed next to one another. Sensor 14' includes a drain 22', a gate 30, and source 24'. Sensor 14" likewise has a drain 22" and gate 30 and shares a common source 24' with sensor 14'. Sensor 14' includes an imprinted layer 32', treated as described above to create a surface that selectively binds with a selected molecule, such as α-defensin, CRP, or other molecule of interest. Sensor 14" includes a non-imprinted layer 32". Non-imprinted layer 32" is formed from the same material as imprinted layer 32', but the non-imprinted layer is not exposed to the molecule of interest when it was formed. Thus, non-imprinted layer 32" does not have cavities shaped to bind with the molecule of interest. The two sensors are located adjacent one another and are formed with very similar electrical characteristics in a manner well-known to those of ordinary skill in the field of semiconductor fabrication. Thus, the chemical environment at the surface of the sensors, as well as their electrical characteristics are nearly identical.

FIG. 5b shows a circuit that forms a differential amplifier. The common source 24' of sensors 14' and 14" is connected with voltage source 35 by current limiting resistor 40. The drain 22' of sensor 14' is connected to ground via resistor 42 and also with the non-inverting input of operational amplifier 48. The drain 22" of sensor 14" is connected to ground via resistor 44 and also connected with the inverting input of operational amplifier 48. According to one embodiment, resistors 42 and 44 are matched so that the voltage drop across each is proportional to the current flowing through the respective sensors 14', 14" and so that the output of amplifier 38 is proportional to the difference in current flowing through sensors. When sensors 14' and 14" are exposed to bodily fluid including the molecule of interest, the molecule will bind with the imprinted surface 32' of sensor 14', changing the gate potential and thus the current flowing through the transistor. Because non-imprinted layer 32" does not bind with the molecule of interest, current flowing through sensor 14" will be unchanged. By providing matched sensors in close proximity to one another changes in the body, for example, changes in pH, osmolarity, fluid conductivity, temperature, etc. will have the same effect on both sensors and will not result in a differential signal from amplifier 48.

In embodiments where a potentiometer forms the circuitry to detect binding of the analyte molecule with the surface, imprinted layers 32' and 32" are formed on working electrodes of the potentiometers. A signal for detecting the presence of the analyte is determined by monitoring a differential signal between the potentiometers.

According to another embodiment instead of, or in addition to, providing a differential measurement using two working electrodes connected with two potentiometer circuits, the potentiometer is provided with a reference electrode in electrical communication with the synovial fluid surrounding the joint. In one embodiment, the reference electrode is provided by the metallic body of the tibial portion of the prosthetic implant itself. The signal generated by the binding of the analyte to the implanted sensor surface is monitored by detecting s potential difference between the sensor working electrode and the reference electrode.

Figure 6:
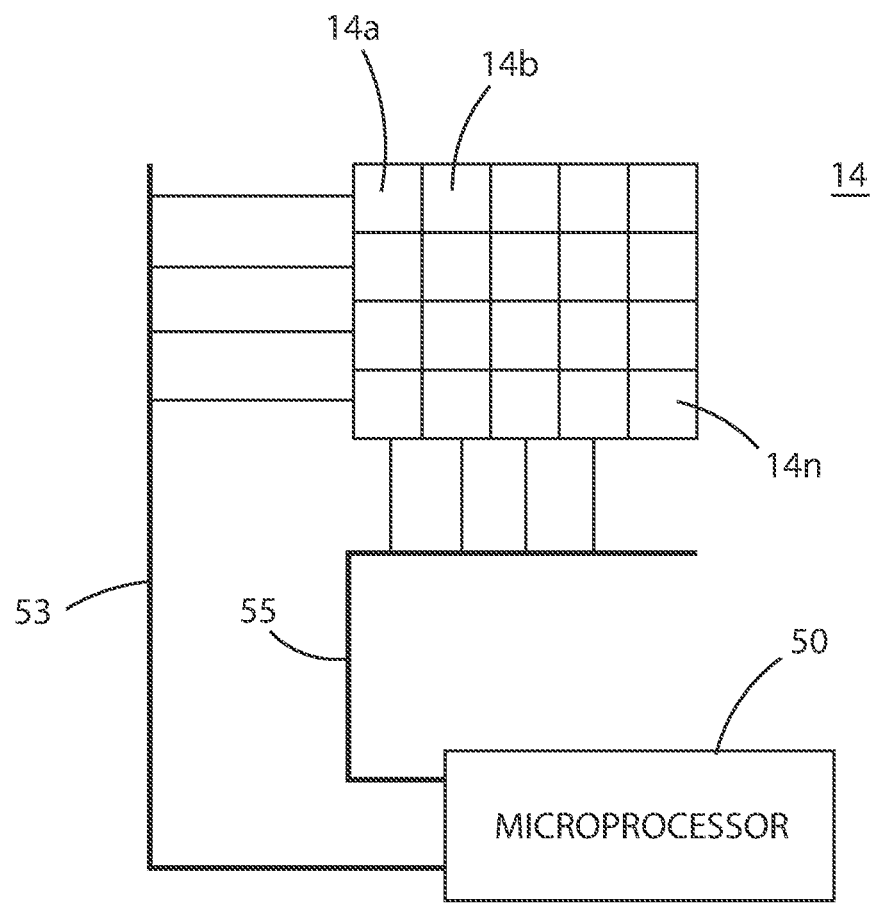
FIG. 6 is a block diagram showing a sensor array according to an embodiment of the disclosure.

FIG. 6 shows another embodiment of the disclosure. Sensor 14 consists of an array of sensors 14a, b, . . . n. Microprocessor 50 is connected with the array 14 via busses 55 and 54. Sensors 14a, b, . . . n each include a gate and sensing surface as described above. The sensing surface may be selectively imprinted to detect one or more molecules of interest, or a combination of such molecules. By selectively reading sensors connected with busses 55, 54, the microprocessor can detect signals from each of the sensors 14a, b, . . . n individually.

Figure 7A:
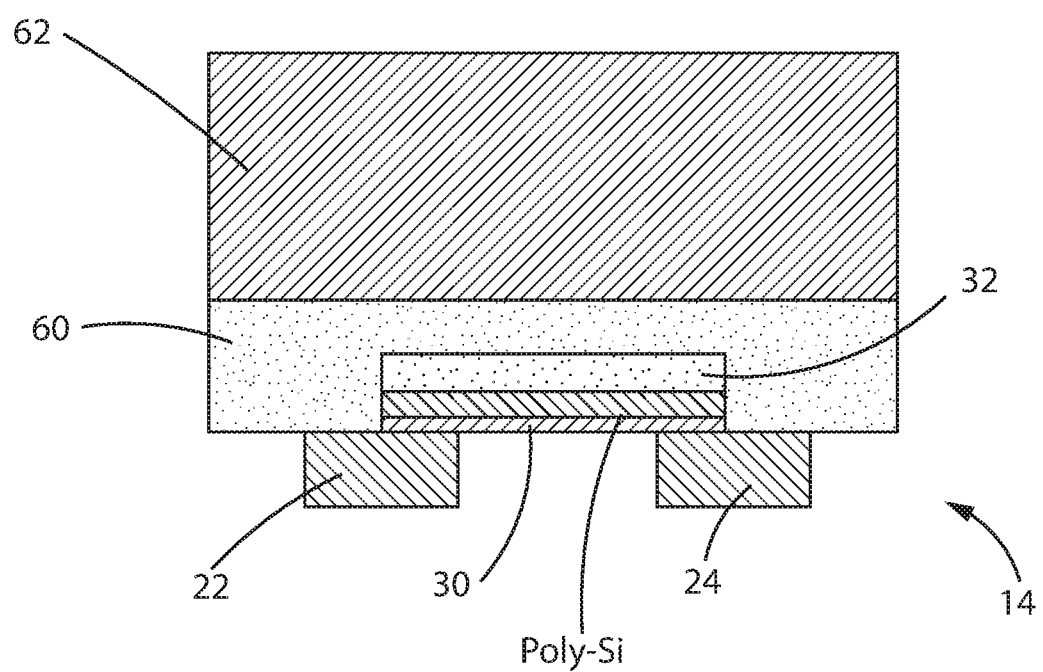
FIGS. 7a and 7b show sensors according to an embodiment of the disclosure.

After prolonged exposure to bodily fluids, one or more sensors 14a, b, . . . n may degrade in performance, for example, because binding sites imprinted on their expose surfaces are all occupied by a molecule of interest or because the patient's cells have covered portions of the sensor. FIG. 7a shows a further embodiment of the disclosure. A dissolvable layer 60, 62 is provided to isolate the imprinted layer 32 of the sensor 14 from bodily fluids for a period of time. Sensor 14 may be formed as described above, including by providing a source 22, drain 24 and gate 30 on a silicon substrate. A sensing layer 32, also formed as described above, is formed on gate 30. Deposited over the gate 30 and sensing layer 32 are one or more layers 60, 62 of materials that are biocompatible and that dissolve in bodily fluid. Layers 60, 62 may be formed from a saccharide with a known dissolution rate. According to one embodiment, a slowly dissolving layer 62 is provided on top of a rapidly dissolving layer 60. This arrangement delays exposure of the sensor 14 for a period of time, for example, a week, a month, or a year. When the slowly dissolving layer 62 dissolves, the rapidly dissolving layer causes the entire surface of sensor 14 to be completely exposed over a short period of time. This arrangement is thought to prevent a vestige of the slowly dissolving layer 62 from interfering with detecting the molecule of interest.

Figure 7B:
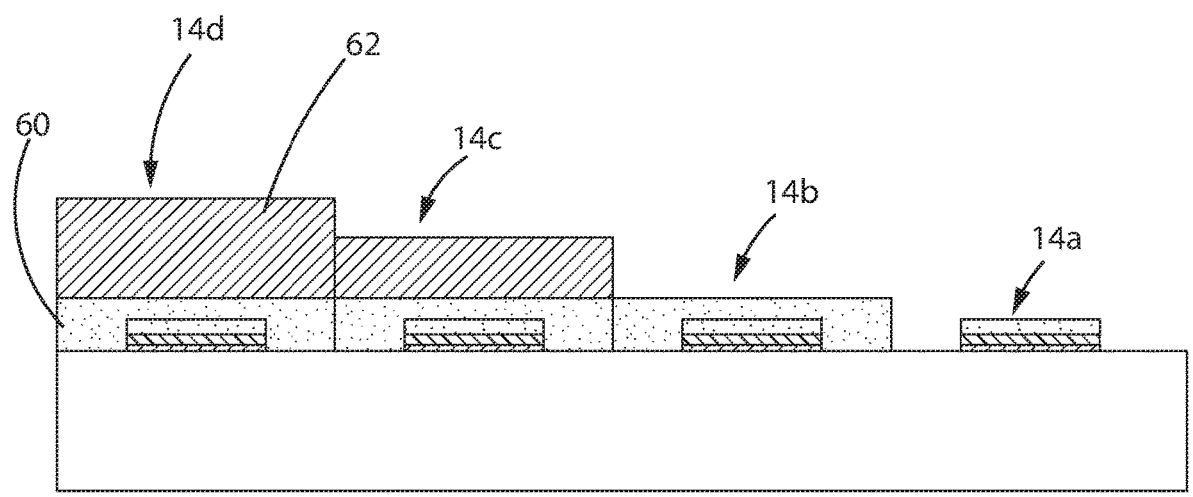

FIG. 7b shows a further embodiment of the disclosure where an array of sensors 14a, b, . . . n is provided. The sensors are covered with slowly and rapidly dissolving layers 62 and 60 respectively. According to this embodiment, different thicknesses of the slowly dissolving layer 62 are provided over different sensors 14a, b, . . . n. As a result, the sensors are exposed sequentially. For example, sensor 14a may be provided with no dissolvable layer. When the device is implanted, sensor 14a functions immediately to detect the presence of a molecule of interest. Sensor 14b has a layer of slowly dissolving material 62 that is designed to dissolve and expose the sensor after a first period of time, for example, one week. Sensor 14c has a thicker layer of material 62 designed to expose the sensor after a longer period of time, for example, two weeks, and so on. Instead of, or in addition to, using layers 62 of differing thicknesses, layer 62 may be made from different materials, for example, saccharides with differing molecular weights to provide a range of dissolution times. A microprocessor 50, as shown in FIG. 6 may be used to select which of the sensors 14a, b, . . . n is selected as being most recently exposed, and therefore the sensor that can provide the most reliable signal indicating the presence of the molecule of interest. According to one embodiment, the microprocessor 50 selects the most reliable sensor based on the elapsed time since the device is first exposed to bodily fluids.

Figure 8:
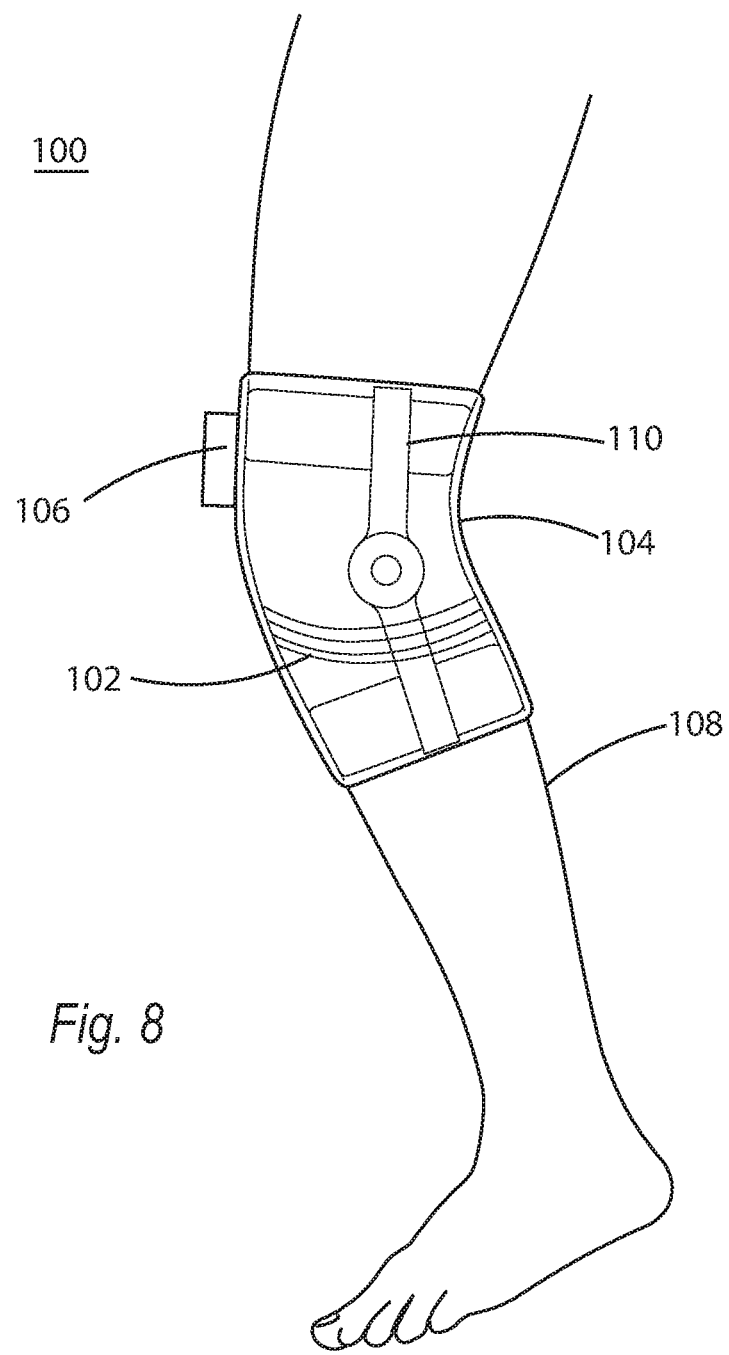
FIG. 8 shows an embodiment of the disclosure worn by a user.

FIG. 8 shows a further embodiment of the disclosure. A post-surgical brace 100 is provided to fit around the patient's leg 108 following the implantation of a prosthesis, such as the one shown in FIG. 1. The brace includes an elastic support band 104 to provide compression to the surgical site, should the patient's physician decide that such compression would help with healing. Brace 100 may also include an orthopedic mechanical support 110, again if the patient's physician determines that such mechanical support is needed to assist with healing. A coil 102 is embedded in the elastic portion of the brace 104 at a location that is approximately co-planar with the top portion of the tibial portion of the implant 1. This arrangement places coil 102 approximately in the same plane with and concentric with coil 18.

Figure 9:
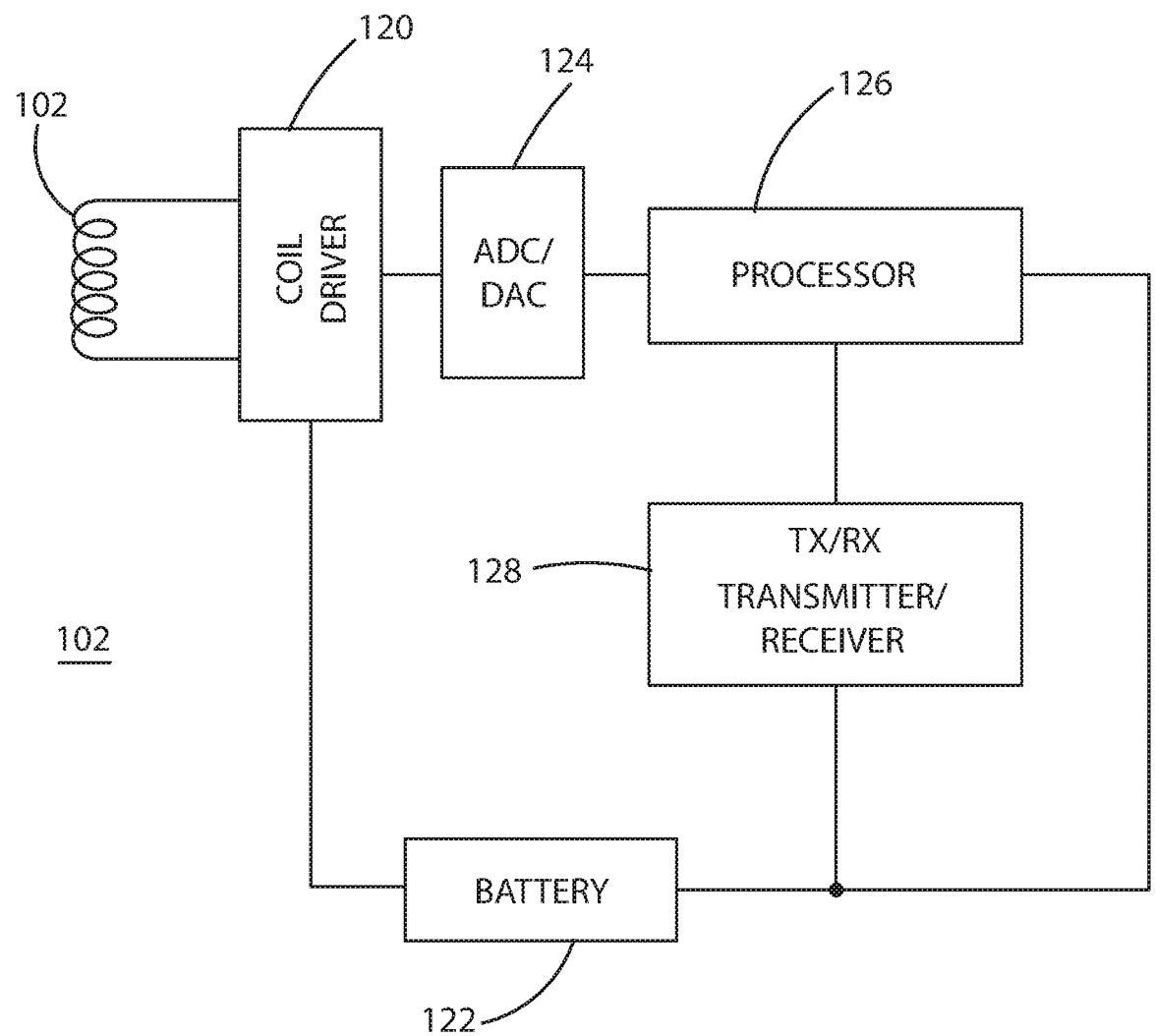
FIG. 9 is an electrical schematic according to an embodiment of the disclosure.

An electronics package 106 is provided on the brace 100. The electronics package 106 includes circuitry connected with coil 102. FIG. 9 shows an exemplary embodiment of the electronics package 102. Coil 102 is connected with coil driver 120. Coil driver 120 may be a voltage-controlled oscillator. Battery 122 provides power to coil driver 120. Coil driver 120 delivers an alternating current signal to coil 102. Coils 102 and 18 are designed to efficiently couple with one another to facilitate the transfer of electrical power from the electronics package to the circuitry 16 on the implant 1. The frequency of the alternating current is selected based on the mutual coupling of coils 102, 18. Processor 126 is connected with coil driver 120 by an analog-to-digital and digital-to-analog converter ADC/DAC 124. ADC/DAC 124 allows the processor 124 to modulate the amplitude, frequency, and phase of the signal sent to coil 102. According to one embodiment, signals are communicated between processor 50 on the implant 1 and processor 126 by modulating the frequency or phase of the signal delivered by the coil driver 120.

A transmitter/receiver (TX/RX) 128 is connected with the processor 126. TX/RX 128 communicates signals to and from processor 126 using any one of a number of known communication systems, including by WiFi, Bluetooth™, ZigBee™ or other communication protocols. Signals from processor 50 indicating that a substance like α-defensin is present in the patient's synovial fluid can this be communicated to a device, such as a cell phone, that can alert a patient or the patient's physician. In response, the physician can take appropriate action, such as by aspirating a sample of fluid to confirm the diagnosis of PJI and beginning a course of antibiotics or other treatment to address the infection.

Figure 10:
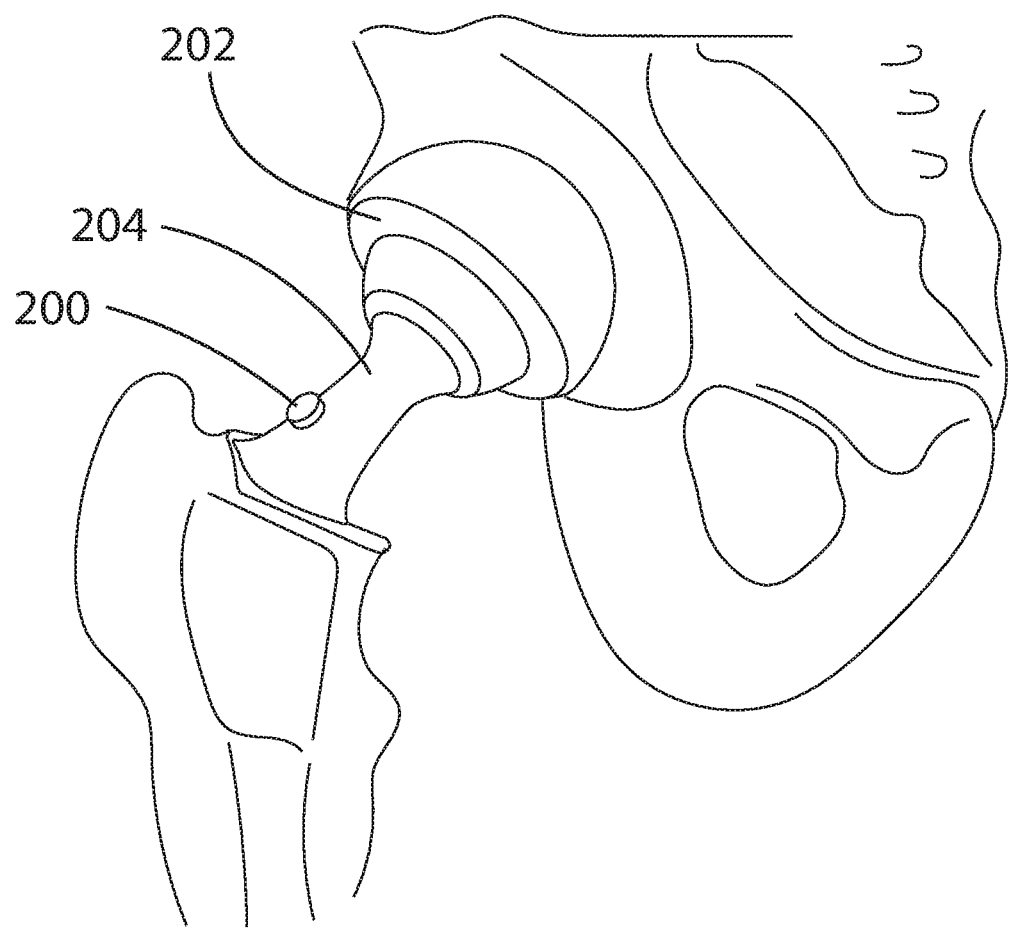
FIG. 10 shows a perspective view of a hip implant prosthesis according to yet another embodiment of the disclosure.

FIG. 10 shows a further embodiment of the disclosure. An acetabular cup 202 is implanted in a patient's pelvis. The cup is joined to a femoral implant 204 implanted in a prepared portion of the patient's femur bone. The cup 202 and femoral implant 204 form an artificial hip provided during a total hip replacement (THR) procedure. A device 200 for detecting analytes that indicate an infection is provided on the stem of the femoral implant 204. The location of the device 200 is selected to become embedded in the pseudo-capsule formed by scar tissue following the THR procedure. This pseudo-capsule surrounds the repaired joint and collects synovial fluid. In response to an infection, substances such as α-defensin, may accumulate in the synovial fluid. As described above, the α-defensin binds with molecular imprinted regions on the sensor, generating an electrical signal that is detected by the circuitry to generate a signal that can be read from outside the patient's body.

According to a further embodiment, sensor 200 can also include surfaces designed to generate an electrical signal when contacted by other substances that indicate an unhealthful condition, such as metal ions including cobalt that can result when metal-on-metal contact occurs with joint implants, such as hip and knee prostheses.

According to still a further embodiment, a sensor, such as described above, is implanted in other area of the body to detect infection or other unhealthy conditions. For example, a device can be implanted in a body space such as the bladder, the sinus cavity, or peritoneum. The device includes a molecularly implanted surface to detect an analyte associated with infection and generate a signal detected outside the patient's body. In one embodiment, the device is implanted in the peritoneum during surgery to repair a bowel injury. The sensor is implanted with a protein that indicates the presence of an infections organism such as *E. coli*. If the organism is detected, this may show that the repaired bowel has failed, allowing leakage of fecal matter into the peritoneal cavity. By providing early detection of this dangerous condition, a repair can be performed quickly, avoiding a potentially dangerous infectious condition.

While illustrative embodiments of the disclosure have been described and illustrated above, it should be understood that these are exemplary of the disclosure and are not to be considered as limiting. Additions, deletions, substitutions, and other modifications can be made without departing from the spirit or scope of the disclosure. Accordingly, the disclosure is not to be considered as limited by the foregoing description.

We claim:

1. A device for detecting infection comprising:
   a sensor configured to be positioned in a body cavity in contact with a body fluid;
   a monitoring circuit, the circuit connected with the sensor and adapted to monitor a signal from the sensor, the signal indicating the presence of one or more analyte compounds in the body fluid, the compounds being associated with a bodily response to an infection;
   a wireless communication transmitter, the transmitter coupled with the circuit and adapted to transmit a signal indicating that the one or more compound is detected,
   wherein the sensor comprises a sensor region reactive to the presence of the analyte,
   wherein the sensor region is covered by the bio-absorbable layer,
   wherein the bio-absorbable layer comprises a rapidly dissolving layer overlying and adjacent to the sensor region and a slowly dissolving layer overlying and adjacent to the rapidly dissolving layer,
   wherein contact with the body fluid by the slowly dissolving layer causes the slowly dissolving layer to be removed after a first period of time to expose the rapidly dissolving layer to the body fluid, and
   wherein contact with the body fluid by the rapidly dissolving layer causes the rapidly dissolving layer to be removed from the sensor region after a second period of time, the second period of time being shorter than the first period of time.

2. The device of claim 1, wherein the sensor comprises an extended or floating gate field effect transistor or a working electrode of a potentiometer, and a molecular imprinted layer, wherein the imprinted layer is electrically coupled with a working electrode of the potentiometer or an extended or floating gate of the field effect transistor.

3. The device of claim 2, wherein the molecular imprinted layer is comprised of a thiol.

4. The device of claim 2, wherein the sensor is a floating gate transistor.

5. The device of claim 2, wherein the molecular imprinted layer is imprinted to preferentially couple with a protein.

6. The device of claim 5, wherein the protein is human α-defensin.

7. The device of claim 5, wherein the protein is C-reactive protein.

8. The device according to claim 2, wherein the sensor comprises two field effect transistors, wherein the molecular imprinted layer is disposed on a gate of one of the two transistors and a non-imprinted layer is formed on a gate of the other of the two transistors, and wherein the sensor detects a differential signal between the transistors.

9. The device of claim 1, wherein the sensor comprises a gold layer and self-assembling molecules, the self-assembling molecules each comprising a thiol group and a hydrocarbon chain, the thiol groups binding with the gold layer and the hydrocarbon chain forming one or more hydrogen bonds with the analyte compound.

10. The device of claim 1, wherein the sensor is coupled with a joint implant.

11. The device of claim 10, wherein the joint implant is a prosthetic knee implant, elbow implant, hip implant, or spine implant.

12. The device of claim 1, wherein the body fluid is synovial fluid.

13. The device of claim 1, wherein the sensor comprises a plurality of sensors, wherein each sensor is adapted to monitor a different one of said one or more compounds.

14. The device of claim 1, further comprising a plurality of bio-absorbable layers, wherein the sensor comprises a plurality of sensor regions and wherein each of the sensor regions is covered by a corresponding one of the plurality of bio-absorbable layers.

15. The device of claim 14, wherein the first period of time for each of the plurality of bio-absorbable layers is different from one another.

* * * * *